United States Patent [19]

Buell

[11] Patent Number: 4,704,115

[45] Date of Patent: Nov. 3, 1987

[54] DISPOSABLE WASTE CONTAINMENT GARMENT

[75] Inventor: Kenneth B. Buell, Cincinnati, Ohio

[73] Assignee: The Procter & Gamble Company, Cincinnati, Ohio

[21] Appl. No.: 851,864

[22] Filed: Apr. 10, 1986

Related U.S. Application Data

[63] Continuation of Ser. No. 697,531, Feb. 1, 1985, abandoned.

[51] Int. Cl.⁴ .............................................. A61F 13/16
[52] U.S. Cl. ................................................. 604/385 A
[58] Field of Search .................. 604/385.1, 385.2, 387, 604/389, 397

[56] References Cited

U.S. PATENT DOCUMENTS

| Re. 26,151 | 1/1967 | Duncan et al. | |
|---|---|---|---|
| 3,860,003 | 1/1975 | Buell | |
| 4,040,423 | 8/1977 | Jones, Sr. | 604/385.2 |
| 4,490,148 | 12/1984 | Beckestrom | 604/385 |
| 4,496,360 | 1/1985 | Joffe et al. | 604/397 |
| 4,500,316 | 2/1985 | Damico | 604/389 |

*Primary Examiner*—John D. Yasko
*Attorney, Agent, or Firm*—Steven W. Miller; Thomas J. Slone; Richard C. Witte

[57] ABSTRACT

A disposable waste containment garment which is particularly useful and leakage resistant for bedridden incontinent adults. The garment has side-edge-leakage-guard gutters having closed ends, and longitudinally elasticized distal edges. The gutters and the other garment elements are configured and disposed to substantially obviate inversion or unfolding of the gutters during application and use of the garment. The garment is sized and configured so that, when secured on a user, the elasticized distal edges of the gutters will normally extend along the groin regions of the user, and diverge upwardly across abdominal, hip and lower back areas of the user rather than encircling the thighs of the user. The absorbent core of the garment is preferably sufficiently resilient to cause it to stand away from some lower abdominal and hip regions of the user. This, in conjunction with the gutters being sufficiently flexible and elasticized, causes adjacent portions of the gutters to be biased open. These open portions of the gutters are, in fact, reservoirs which substantially obviate leakage by containing free liquid during urination events when fluid is received in the garment faster than it can be absorbed in the absorbent core of the garment, or whenever free liquid is squeezed out of a portion of the garment as when the weight of a bedridden user is shifted. The ends of the gutters in the waistband regions of the garment may be sealed liquid tight, or be secured closed with edge portions of the absorbent core and/or topsheet disposed therein, or a combination of such sealing and securing.

19 Claims, 13 Drawing Figures

DISPOSABLE WASTE CONTAINMENT GARMENT

This is a continuation of application Ser. No. 697,531, filed on Feb. 1, 1985, now abandoned.

DESCRIPTION

1. Technical Field

This invention pertains to waste-containment garments such as disposable briefs for incontinent adults, and diapers. More specifically, it pertains to such garments having structural features which render them highly resistant to leakage even when free liquid (i.e., unabsorbed liquid) is present in the garment.

2. Background Art

U.S. Pat. No. Re. 26,151 which reissued Jan. 31, 1967 (Originally U.S. Pat. No. 3,180,335, dated Apr. 27, 1965) to Robert C. Duncan discloses a Disposable Diaper having inwardly folded side flaps, and means to fasten the ends of the inwardly folded edges of the side flaps in position over the face of the absorbent pad of the diaper. This patent further recites: "It is important that the flaps be unsecured in the crotch area so as to permit them to properly function as previously discussed."

U.S. Pat. No. 3,860,003 which issued Jan. 14, 1975 to Kenneth Barclay Buell, the inventor herein, discloses Contractable Side Portions For Disposable Diapers. Such diapers have outwardly extending side flaps, and elastic members "whereby effective elastic side flaps are formed on the integral diaper and the side flaps being compliant and forming effective seals about an infant's leg."

U.S. Pat. No. 4,490,148 which issued Dec. 25, 1984 to Bo Beckestrom discloses a Protector Against Incontinence Or Diaper that has inwardly folded side flaps that are fixed at their ends to the bottom layer, and which side flaps have elasticized free edges. The Beckstrom patent follows the Duncan teaching that such side flaps be unsecured in the crotch area. Indeed, Beckstrom positions the points of fastening the ends of the side flaps to beyond the waistband edges of the absorbent core, and fastens them to underlying portions of the bottom layer: i.e., the backsheet.

While some of the problems of providing leakage resistant waste containment garments have been at least partially ameliorated by garments disclosed in the background patents, none has solved the problems in the manner of or to the extent of the present invention. For example and not by way of intending to limit the present invention, the present invention has addressed the problem of inversion or outwardly folding of inwardly turned side flaps due to frictional engagement with skin areas of the person on whom the garment is being applied during application of background-art type garments on adult incontinents: particularly bedridden adult incontinents. Accordingly, among other things, the present invention provides a waste containment garment which comprises side-edge-leakage-guard gutters, and means for substantially obviating their inversion during application and use of the garment.

DISCLOSURE OF THE INVENTION

In accordance with one aspect of the invention, a disposable waste containment garment is provided which preferably comprises a body member having a width that is substantially less than one half the girth of a prospective user, and means for securing the garment on such a user. The body member of the garment comprises a liquid permeable topsheet, a liquid impervious backsheet, an absorbent core disposed intermediate the topsheet and the backsheet, and two inwardly facing, longitudinally extending, liquid impermeable side-edge-leakage-guard gutters having proximal and distal edges. The gutters are disposed adjacent the longitudinal side edges of the body member so that their proximal edges are disposed outboard from the absorbent core. The gutters are flexible—preferably portions of the backsheet which is preferably polyethylene film having a thickness of about one mil—and comprise means for being longitudinally elasticized adjacent their distal edges. The garment is sized and configured with respect to prospective users that the distal edges can contact torso areas of users throughout their lengths rather than encircling the thighs of the users: that is, the body member of the garment is so sized and configured that the distal edges of the gutters are substantially precluded from encircling the thighs of users having sizes in the range of sizes for which a given size garment is intended. The means for securing the garment on a user are so configured that laterally directed tension is applied to portions of the proximal edges of the gutters The garment also comprises means for substantially obviating inversion of the gutters during application and use of the garment: preferably by virtue of portions of the distal edges of the gutters being pulled into the groin regions of the user by forces usually applied to the garment as it is being secured on the user. In one preferred aspect of the invention the means for substantially obviating inversion of the gutters comprises means for securing closed, end portions of the gutters disposed in the waistband regions of the garment and for securing closed only sufficiently long lengths of the gutters in the crotch region of the garment to substantially obviate inversion under normal forces encountered when applying the garment to a user, and leaving the remainder length portions of the gutters freely openable: that is, without securing the distal edges of such remainder lengths of the gutters to underlying structure of the garment. In one aspect of the invention only a short length of each gutter adjacent its distal edge is secured to underlying structure in the central crotch portion of the garment: i.e., in the vacinity of the lateral centerline of the absorbent core. In another aspect of the invention only a short length of each gutter adjacent its distal edge that is spaced intermediate the central crotch portion and the rear waistband region is secured to underlying structure. And, in a third aspect of the invention, such short lengths in both the central crotch portion and the latter secured portion are secured closed, in addition to the ends of the gutters being closed, while leaving the remainder lengths of the gutters freely openable. Preferably, all of the ends of the gutters are secured closed at about the elevation of where, when the garment is secured on a seated user, the upper portions of the user's thighs intersect the torso of the user; most preferably closed about edge portions of the absorbent core albeit it is not intended to thereby preclude suitable closure by securing the ends of the gutters closed by securing portions of the gutter to adjacent portions of other garment structure such as the backsheet or topsheet.

BRIEF DESCRIPTIONS OF THE DRAWINGS

While the specification concludes with claims which particularly point out and distinctly claim the subject matter regarded as forming the present invention, it is believed the invention will be better understood from the following descriptions taken in conjunction with the accompanying drawings in which identical features in the several views are identically designated and in which:

DETAILED DESCRIPTION OF THE INVENTION

Figure 1:
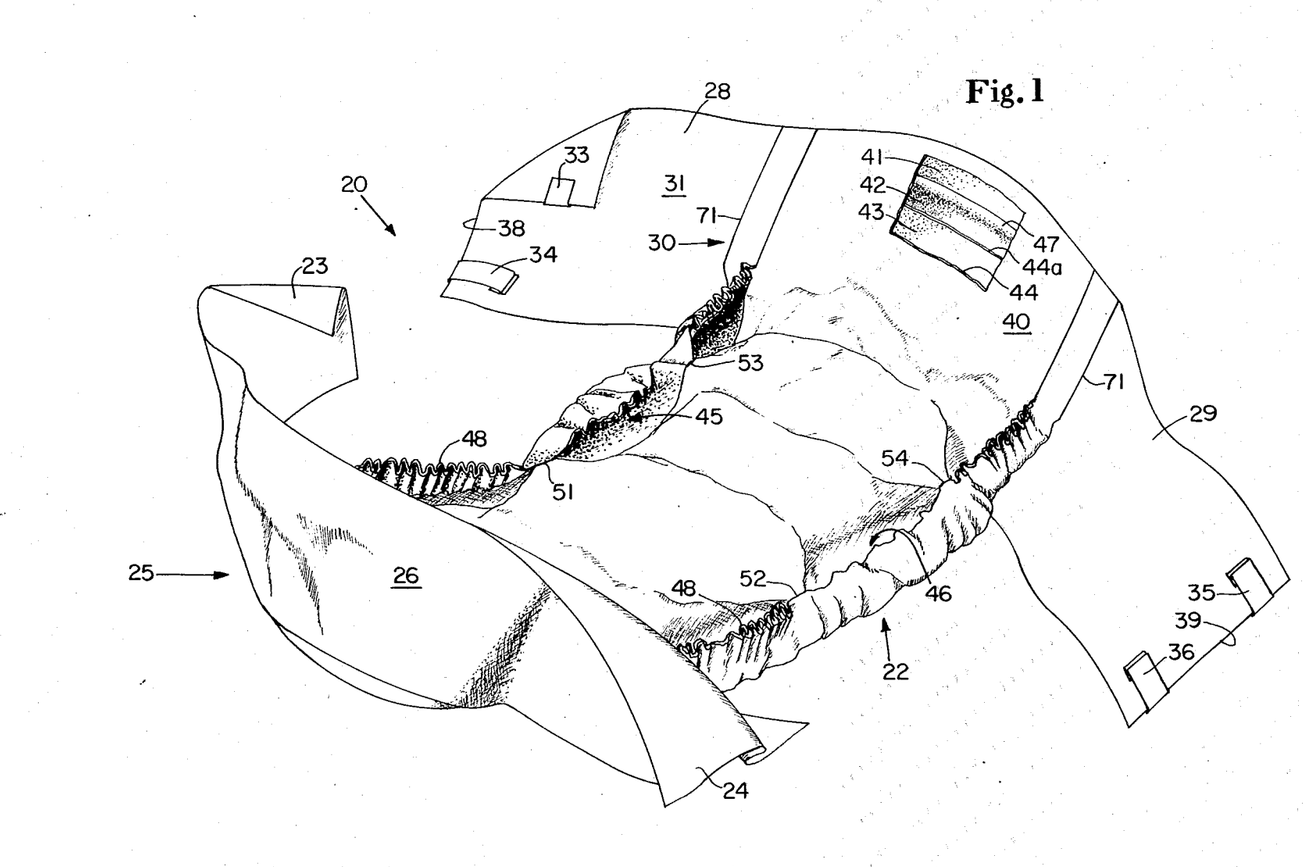
FIG. 1 is a perspective view of a disposable incontinent brief embodiment of the present invention.

An exemplary disposable waste containment garment embodiment of the invention is designated incontinent brief 20 in FIG. 1, and is shown therein to comprise: a body member 22; two stub-belts 23 and 24 which extend laterally outwardly from the front waistband region 25 of body member 22 and which stub-belts 23 and 24 are opposite end portions of a front half-belt 26; two stub-belts 28 and 29 which extend laterally outwardly from the rear waistband region 30 of body member 22 and which stub-belts 28 and 29 are opposite end portions of a rear half-belt 31; and four tape-tab fasteners designated 33 through 36, two each of which are disposed on distal edges 38 and 39 of stub-belts 28 and 29, respectively (i.e., fasteners 33 and 34 adjacent the ends of distal edge 38 of stub-belt 28, and fasteners 35 and 36 adjacent the ends of distal edge 39 of stub-belt 29). As further shown in FIG. 1, body member 22 comprises: a topsheet 40; a backsheet 41; an absorbent core 42 that is enveloped in tissue paper 43 and disposed intermediate topsheet 40 and backsheet 41; and two longitudinally extending side-edge-leakage guard gutters 45 and 46 having distal edges 48 and proximal edges 71. The distal edges 48 are shown to be gathered or contracted by elastic means not shown in FIG. 1. Portions of backsheet 41, and tissue paper 43 are visible through a hole torn in topsheet 40 along tear line 44; and a portion of absorbent core 42, including its rear edge 47, is also visible through that hole because a portion of the tissue paper 43 is also torn away along tear line 44a. Additionally, in the embodiment shown in FIG. 1, four surface areas of the gutters which are disposed adjacent their distal edges are secured to underlying structure (i.e., the topsheet): two of these are designated central gutter closure zones 51 and 52 which are located in the central crotch region of the garment; and the other two are designated rear-quarter gutter closure zones 53 and 54 which are disposed about midway between zones 51 and 52, respectively, and the closed ends of the gutters disposed in the rear waistband region of the garment.

Basically, without intending to limit the present invention by a brief explanation, the present invention is a waste containment garment that, when provided in adult sizes that are commonly referred to as adult incontinent briefs, are especially useful and leakage resistant when applied to bedridden users. This is so because they have relatively narrow body members that are fitted with inwardly facing side-edge-leakage-guard gutters having elasticized distal edges. When the garment is properly fitted and secured on a user, the elasticized distal edges of the gutters run through the groin areas, and diverge upwardly over both the abdomen and the hips/lower back of the user. Additionally, when properly fitted and sized, the proximal edges 71 also lie across hip/back and abdominal areas rather than encircling the thighs of the user or overlapping about the sides of the user. The elasticized edges are also precluded by the size and configuration of the body member from encircling the thighs of the user or overlapping around the sides of the user. Importantly, short lengths of the distal edges of the gutters are secured to underlying structure to obviate their inversion during application and use of the garment. In a preferred embodiment, such securement is adjacent the central crotch region of the absorbent core; and, more preferably, further comprises an additional area of such securement in the rear hip regions of the user. Whereas, friction between the inwardly turned side flaps or gutters and skin areas of user acts to cause such flaps or gutters to be inverted —i.e., folded outwardly—when such garments are being applied to users; particularly when being applied to bedridden patients by attendants. The present invention substantially obviates such inversion by securing minor length portions of such gutters closed while leaving the remainder length portions freely openable. Such a garment is highly leakage resistant—particularly for bedridden users lying on their sides—because the freely openable portions of the gutters act to collect and hold free (unabsorbed) liquid until it is absorbed into the absorbent core of the garment: such liquid usually being at elevations below the adjacent portions of the distal edges of the downside gutter. Accordingly, such a garment can be loosely fitted on a bedridden user for comfort, and still be highly leakage resistant because its elasticized edges do not normally have the function as hydraulic seals. For this reason, such garments are also particularly useful and comfortable when applied to very thin (eg, emaciated) users who sometimes have concave body areas which areas are spanned by but not contacted by portions of the elasticized edges regardless of the degree of tension.

Figure 2:
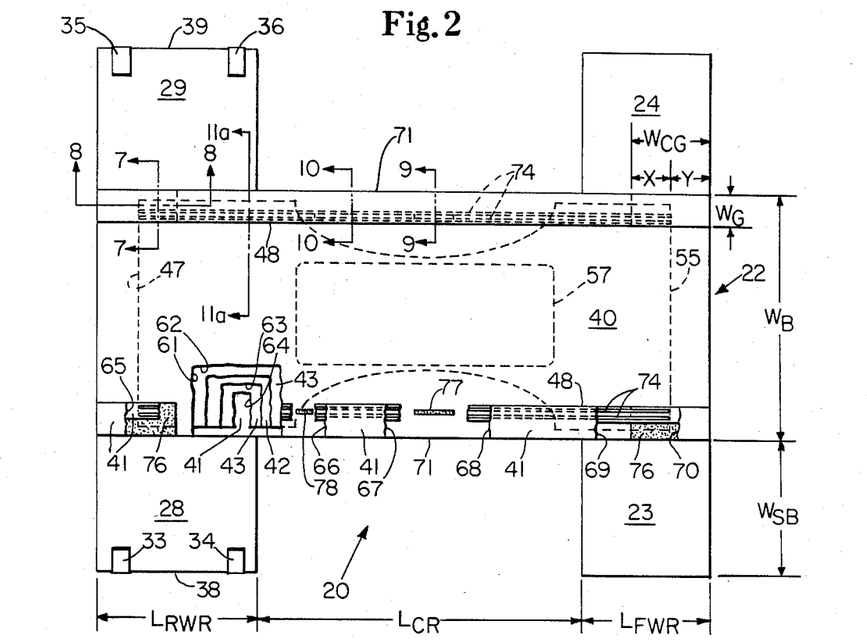
FIG. 2 is a flat-out, plan view of the disposable incontinent brief shown in FIG. 1 with the topsheet thereof facing upwards, and wherein portions have been torn away to more clearly show underlying structure.

Referring now to FIG. 2, incontinent brief 20 of FIG. 1 is shown in the flat-out, uncontracted state with its topsheet 40 facing the viewer. In this view, the edge of the absorbent core is indicated by a dashed-line and designated 55; and a thick portion of the absorbent core is indicated by another dashed-line and designated 57. Additionally, in order to clearly show the construction of brief 20, portions of the topsheet 40, the top layer of tissue paper 43, the absorbent core 42, and the back layer of tissue paper 43 are torn away along tear-lines 61, 62, 63 and 64, respectively; and gutter forming side edge portions of backsheet 41 are torn away along tear-lines 65 through 70. Also, two strands 74 of elastic are disposed along each side of the brief, which strands have only their ends adhesively secured between two folded layers of backsheet 41 adjacent the ends of the absorbent core. In addition, each end of each gutter is sealed closed for a length Y by securing the gutter forming edge portion of backsheet 41 to the underlying area of topsheet 40; and each end of each gutter is secured closed for about a length X about an edge portion of the absorbent core 42 with portions of the top layer of tissue paper 43 and topsheet 40 disposed therebetween. Such gutter end sealing and closure are effected by adhesive areas designated 76, portions of two of which are shown exposed and spackled in FIG. 2. And, two additional areas of adhesive are shown along the right side of brief 20, FIG. 2, and designated 77 and 78. Identical adhesive areas are also provided on the left side of the brief. Adhesive areas 77 and 78 are provided to secure short lengths of the gutters closed to form gutter closure zones 51 through 54, FIG. 1. The lengths of the gutters which are not secured closed (i.e., the ends and the gutter closure zones) are deemed to be freely openable gutter portions.

Still referring to FIG. 2; the portion of the brief having a length $L_{RWR}$ is designated the rear waistband region; the portion having a length $L_{FWR}$ is designated the front waistband region; and the length $L_{CR}$ is designated the crotch region albeit it is not intended to thereby strictly define such regions of the brief. Additionally, to facilitate further describing brief 20: $W_G$, FIG. 2, is the width of each gutter 45, 46, FIG. 1; $W_B$, FIG. 2, is the width of body member 22; $W_{SB}$ is the lateral length of each stub belt; $W_{CG}$ is the length of the closed end of each gutter: i.e., the sum of lengths X and Y as described above.

Figure 3:
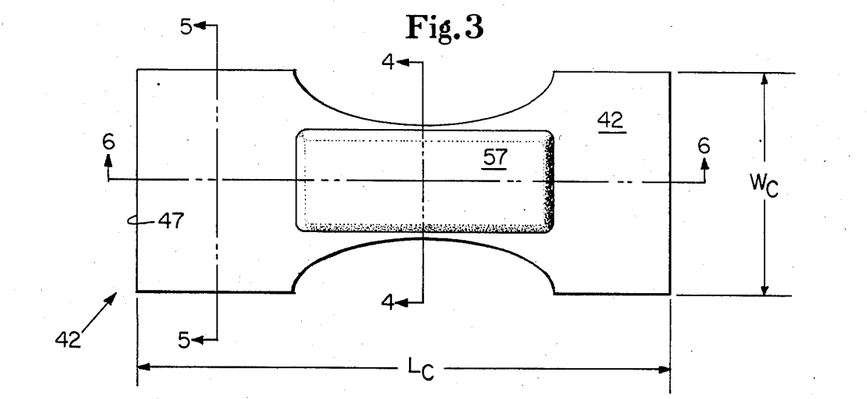
FIG. 3 is a plan view of the absorbent core of the disposable incontinent brief shown of FIGS. 1 and 2.
Figure 4:
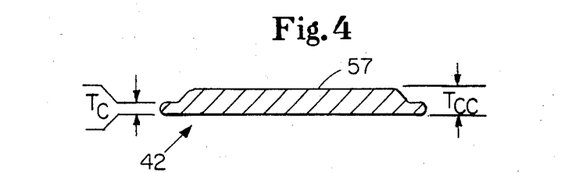
FIGS. 4, 5 and 6 are sectional views taken along section lines 4—4, 5—5 and 6—6, respectively, of FIG. 3.
Figure 5:
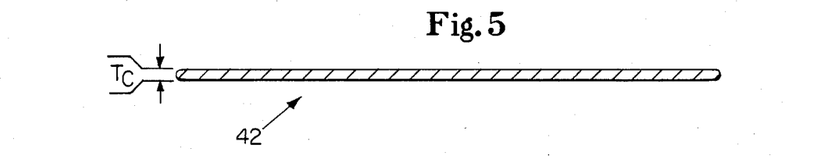
Figure 6:
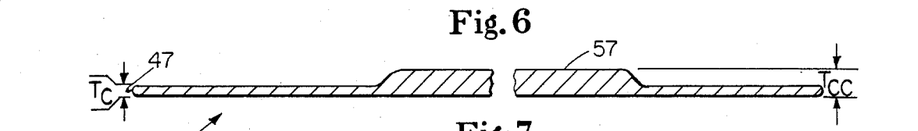

Absorbent core 42, FIG. 3, of brief 20, FIG. 1, is somewhat hourglass-shape; has a width designated $W_C$; and length $L_C$. As further shown in FIGS. 4 through 6, portion 57 of core 42 is thicker (i.e., thickness $T_{CC}$) than the remainder of the core (i.e., thickness $T_C$). Preferably, the core is airfelt albeit it is not intended to thereby limit the present invention. Such a core has a propensity to be folded along the laterally extending end edges of portion 57.

Figure 7:
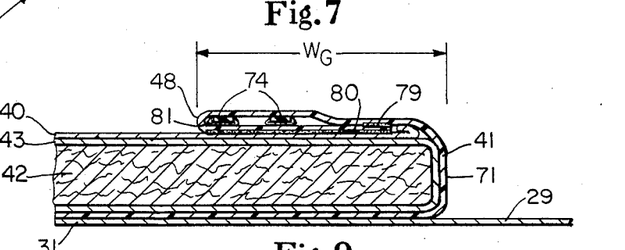
FIGS. 7, 8, 9 and 10 are enlarged scale, fragmentary sectional views taken along section lines 7—7, 8—8, 9—9 and 10—10, respectively, of FIG. 2, and wherein thicknesses have been exaggerated to more clearly depict the construction.

FIG. 7 is a fragmentary sectional view along section line 7—7 of FIG. 2 and shows—with exaggerated thicknesses and in enlarged scale—that core 42 is enveloped in a full wrap of tissue paper 43; that topsheet 40 substantially covers the entirety of core 42 and has its edge secured to an adjacent area of backsheet 41; that backsheet 41 is U-folded about the edge of the wrapped core to overlie the topsheet 40, and that an edge portion of backsheet 41 is U-folded back on itself to enclose strands 74 of elastic in a tunnel that is sealed by adhesive 79. The juxtaposed areas of the topsheet 40 and the backsheet 41 are adhesively secured together by adhesive 80; and the ends of the strands 74 of elastic are secured in the backsheet-formed-tunnel by adhesive 81. Additionally, a portion of the rear half-belt 31 is shown secured to backsheet 41 so that stub-belt 29 extends laterally outwardly from edge 71.

Figure 8:
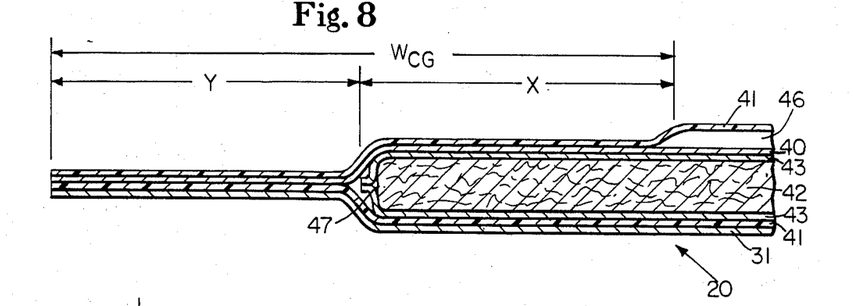

FIG. 8 is a fragmentary, longitudinal sectional view taken along section line 8—8 of FIG. 2 which shows—with exaggerated thickness and in enlarged scale—the construction of brief 20 along a side edge portion thereof. As stated hereinbefore, all of the plies over length $W_{CG}$ are secured together as with, for example, adhesives; and, to the right of length $W_{CG}$ as shown in FIG. 8, the portion of backsheet 41 that is superjacent topsheet 40 is not secured thereto. Thus, it depicts a slightly open freely-openable-portion of gutter 46.

Figure 9:
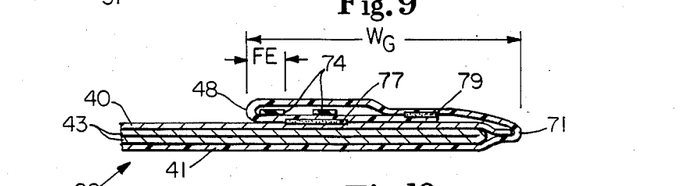

FIG. 9 is a fragmentary sectional view along section line 9—9 of FIG. 2 and shows—with exaggerated thicknesses and in enlarged scale—the edge/gutter construction of body member 22 in the central crotch region where the gutter forming portion of backsheet 41 is secured to the topsheet 40 by adhesive 77. As previously stated, the strands 74 of elastic are preferably not secured to the adjacent areas of the backsheet through this zone. In this view, it is clear that adhesive 77 is spaced a distance FE from distal edge 48.

Figure 10:
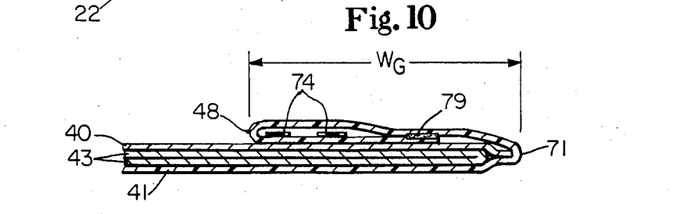

FIG. 10 is a fragmentary sectional view along section line 10—10 of FIG. 2 and shows—with exaggerated thicknesses and in enlarged scale—the edge/gutter construction of body member 22 in a freely openable span of gutter: i.e., a span wherein the portion of the backsheet 41 that overlies the topsheet 40 is not secured thereto.

Figure 9A:
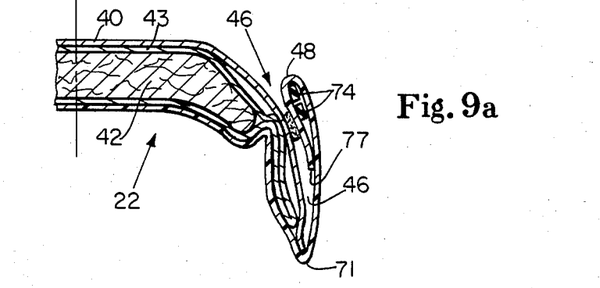
FIGS. 9a, 10a and 11a are enlarged scale, fragmentary sectional views of a disposable incontinent brief of the configuration shown in FIGS. 1 and 2 with the brief secured on a user, the sectional views being taken along sectional lines aligned with section lines 9—9, 10—10 and 11—11 respectively, of FIG. 2; and in which views thicknesses have been exaggerated as in FIGS. 7 through 10 to more clearly depict the construction.
Figure 10A:
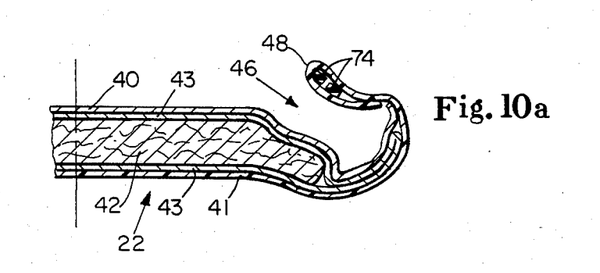
Figure 11A:
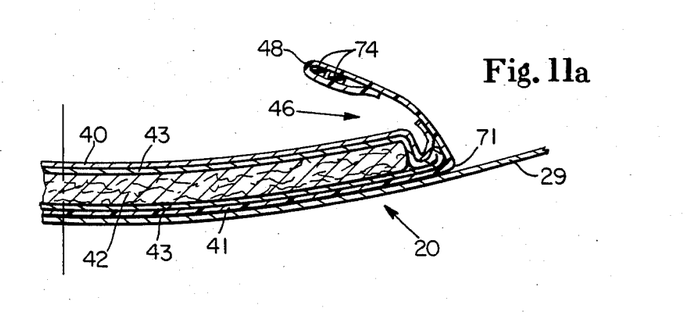

FIGS. 9a, 10a and 11a are fragmentary lateral sectional views which depict an incontinent brief 20, FIG. 1, as it might be shaped when applied to a user, albeit thicknesses of some of the components have been exaggerated for clarity. In particular, FIG. 9a depicts gutter 46 facing upward (i.e., cupped downward) and oriented as it would be with the distal edge 48 of the gutter disposed along the left groin of the user, and the outside surface of the gutter extending downward along the inner thigh of the user; and with the absorbent core portion spanning the perineum of the user. In a similar vein, FIG. 10a depicts a lateral section disposed rearward from the section of FIG. 9a, and shows th gutter 46 standing substantially open: ready to catch and contain free (i.e., unabsorbed) liquid until it can be wicked into and absorbed into adjacent portions of the absorbent core 42. Additionally, this view clearly shows that the gutter would so contain free liquid whether the user was disposed on his or her side, or erect as when seated or standing. This view also clearly shows that the gutter 46 is partially lined by wicking material: i.e., the plies of tissue paper 43 which are disposed between the liquid pervious topsheet 40 and the liquid impervious backsheet 41. Such wicking-material lining extends throughout the lengths of the gutters and, therefore, the gutters are said to be coherently lined with liquid wicking material.

FIG. 11a depicts the lateral section of brief 20 in the lower left back portion of a user. In this view, it is clear that lateral tension in the stub-belt applies lateral tension to the proximal edge 71 of gutter 46; and that gutter 46 is substantially open with its distal edge 48 disposed inboard from proximal edge 71. As stated hereinabove, this geometry provides effective leakage protection even for users who are lying on their sides by providing reservoirs to catch and contain free liquid until it is absorbed into core 42.

Exemplary Embodiment

An exemplary medium-size embodiment of brief 20 that is well suited for users having waist or hip sizes in the range of from about twenty-six inches (about 66 cm) to about forty-six inches (about 117 cm), but more preferably in the range of from about twenty-eight inches (about 71 cm) to about forty-four inches (about 112 cm), is manually constructed as follows albeit it is not intended to thereby limit the present invention.

The backsheet 41 is made from a sheet of polyethylene having a thickness of about one mil, and which is about seventeen inches wide by about thirty-one inches long (about 43 cm by 79 cm). With the backsheet restrained in the flat-out position, strands 74 of elastic are stretched about one-hundred-twenty-five percent, and then only their ends are adhered to the backsheet about four inches (about 10 cm) from each end. They are spaced so that the strands 74 nearest the side edges are spaced about one-and-one-eighth inches (about 3 cm) therefrom; and the inboard strands 74 are spaced about three-eighths of an inch (about 1 cm) center-to-center therefrom. Then, longitudinal edge portions about one inch wide (about 2.5 cm) are U-folded up and inwardly over the elastic strands 74 and the distal edge portions of those longitudinal edge portions are secured throughout their lengths to subjacent areas of the backsheet. The longitudinal edges formed by these U-folds ultimately become the distal edges 48 of the gutters 45 and 46, as previously designated. The backsheet is then ready to have the absorbent core assembly joined with it.

The absorbent core assembly comprises an absorbent core 42 that is fully enveloped and sealed within tissue paper 43. The plan form of the envelope of tissue paper is preferably rectangular albeit the core 42 preferably is hourglass-shape as shown in the figures. The absorbent core assembly has a width of about eleven inches (about 28 cm) and length of about twenty-seven inches (about 69 cm). It is secured to the backsheet with adhesive or double sided tape or the like so that its ends are about two inches (about 5 cm) from each end of the backsheet, and with equal width side-edge portions (i.e., gutter forming portions) of the backsheet 41 exposed on each side.

The absorbent core assembly is then covered by the topsheet which has a length equal to the length of the backsheet, and a width of about twelve inches (about 30.5 cm). Its edge portions which extend beyond the edges of the absorbent core assembly are then secured to underlying areas of the backsheet. The gutter forming edge portions of the backsheet are then U-folded along the longitudinal edges of the absorbent core assembly; and secured by adhesive in areas 76, FIG. 2, in each corner, and the adhesive areas 77 and 78 adjacent each distal edge 48 as previously described. The longitudinal edges formed by these last U-folds are alternatively designated longitudinal side edges or proximal edges 71. This completes the assembly of the body member 22 of brief 20.

The body member 22 of brief 20 is then turned over and the half-belts 26 and 31 are secured thereto in the positions indicated in the drawings. In the exemplary embodiment, the half-belts are two ply laminates: an outer lamina of polyethylene film such as used for the backsheet 41; and an inner lamina of nonwoven polypropylene. Both half-belts have a lateral dimension of about twenty-five inches (about 63.5 cm); and the front half-belt 26 and the rear half-belt 31 have longitudinal lengths (i.e., the heights of the front and rear waistband regions, respectively) of about six inches (about 15 cm) and about eight inches (about 20 cm), respectively. The factory bond ends of adhesive tape-tab fasteners 35 through 38 are secured to the four corners of the back half-belt 31 as shown in FIGS. 1 and 2 to complete the assembly of brief 20.

While the construction of the exemplary brief 20 has been described as comprising laminated half-belts, four discrete stub belts could obviously be utilized, and they could be made entirely from air permeable material to be breathable. However, it is not intended to limit the present invention to construction having four stub-belts. Additionally, while the above described construction provides gutters having widths $W_G$, FIG. 2, of about one-and-one-half inches (about 4 cm), the preferred range of gutter widths is from about three-quarters-of-one-inch (about 2 cm) to about three inches (about 7.6 cm); and the more preferred range is from about one inch (about 2.5 cm) to about two inches (about 5 cm).

The brief 20, is applied to a user—for example a bedridden person—by positioning the rear waistband region 30 under the person's back, and drawing the remainder between the person's legs so that the front waistband region 25 is positioned across the front of the person. The user's-bond ends of the tape fasteners are then secured: preferably to outwardly facing areas of the front stub-belts 23 and 24. In this manner, attachment tension in the stub-belts is positively applied to the proximal edges 71 of the portions of the gutters disposed in the waistband regions of the brief. This, acts in conjunction with the elasticized distal edges 48 of the gutters to provide the gutter dispositions and functions described hereinbefore. When so applied, the distal edges of the gutters extend through the groin regions, and up the lower back and the abdomen of the user; and the proximal edges also lie on the lower back and abdomen of the user. Neither the proximal nor the distal edges encircle the thighs of the user or extend in overlapping relation around the sides of the user.

When such a garment is fitted on a user, the thickness of the region 57 of absorbent core 42, and the fact that the elastic strands 74 are only secured at their ends and extend through tunnels along the distal edges of the gutters, induces folding of the garment along the lateral end edges of region 57; and gathers the portions of the gutter disposed outboard therefrom much more so than adjacent the central crotch region. This is depicted in FIG. 1 by depicting highly gathered portions of the distal edges 72 as being scalloped; while not so scalloping the lesser gathered portions. This provides a high degree of elongation-contraction where it is most needed, i.e., in the lower rear hip regions of the wearer when the user's geometry changes significantly as the user sits, walks, etc.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable waste containment garment having a rear waistband region, a front waistband region, and a crotch region, said garment comprising:
   a liquid permeable topsheet;
   a liquid impervious backsheet;
   an absorbent core disposed intermediate said topsheet and said backsheet;
   two inwardly facing, longitudinally extending, liquid impermeable side-edge-leakage guard gutters having proximal and distal edges, said gutters being disposed adjacent the longitudinal side edges of the garment;

means for longitudinally elasticizing said gutters adjacent said distal edges, the garment being sized and configured with respect to the user to enable said distal edges to contact torso areas of the user throughout the lengths of said distal edges and to substantially preclude said distal edges from encircling the thighs of the user;

means for securing the garment on the user so that laterally directed tension is applied to portions of said proximal edges of said gutters which extend between the ends of the garment and the upper thigh elevation of the user; and means for substantially obviating inversion of said gutters during application and use of the garment.

2. The disposable waste containment garment of claim 1 wherein said means for substantially obviating inversion of said gutters during application and use of the garment comprises means for securing closed, end portions of said gutters disposed adjacent the waistband regions of the garment.

3. The disposable waste containment garment of claim 2 wherein said means for securing closed, end portions of said gutters are disposed about edge portions of said absorbent core.

4. The disposable waste containment garment of claim 3 wherein said means for securing closed, end portions of said gutters are disposed beyond the end edges of said absorbent core such that the ends of said gutters are sealed closed beyond the end edges of said absorbent core.

5. The disposable waste containment garment of claim 2 wherein said means for substantially obviating inversion of said gutters additionally comprises means for securing closed a first length portion of each of said gutters in the central crotch region of the garment.

6. The disposable waste containment garment of claim 2 or 5 wherein said means for substantially obviating inversion of said gutters additionally comprises means for securing closed a second length portion of each of said gutters disposed intermediate the central crotch region and the rear waistband region of the garment, the remaining length portions of said gutters being freely openable.

7. The disposable waste containment garment of claim 6 wherein said gutters are sufficiently flexible and elasticized that, when the garment has been secured on the user, some freely openable length portions of said gutters are biased open.

8. The disposable waste containment garment of claim 1 wherein said means for securing the garment on the user comprises tape tab fasteners that apply laterally directed tension to portions of said proximal edges of said gutters that are disposed adjacent the waistline of the user and adjacent both leg-torso junctures of the user.

9. The disposable waste containment garment of claim 1 wherein said means for securing the garment on the user comprises stub belt members disposed at both corner of at least one end of the garment and which stub belts extend laterally outwardly from the proximal edge regions of adjacent portions of said gutters and means for securing distal edge portions of both of said stub belt members to the garment so that the entire girth of the user is encircled by a composite of tensioned portions of the said stub belt members and waistband portions of the garment.

10. The disposable waste containment garment of claim 9 wherein stub belt members are disposed at both corners of both ends of the garment.

11. The disposable waste containment garment of claim 9 or 10 wherein said stub belt members comprise air permeable material.

12. The disposable waste containment garment of claim 1 wherein said gutters are formed from longitudinally extending edge portions of said backsheet.

13. The disposable waste containment garment of claim 12 wherein said backsheet has a width sufficiently greater than the width of said topsheet to provide longitudinally extending side-gutter-forming edge portions outboard from the longitudinal edges of said topsheet, said backsheet being U-folded adjacent the longitudinal side edges of said topsheet so that said edge portions overlie longitudinal side edge regions of said top sheet, said edge portions and said side edge regions being secured together in face-to-face relation only in the waistband regions of the garment and in the attachment zone that is disposed adjacent each longitudinal edge of said garment intermediate said waistband regions.

14. The disposable waste containment garment of claim 1 wherein said gutters are formed from longitudinally extending edge portions of said topsheet which are liquid impermeable.

15. The disposable waste containment garment of claim 1, 12, 13, or 14 wherein said gutters are coherently lined at least in part throughout their entire lengths with liquid wicking material.

16. The disposable waste containment garment of claim 1 wherein said means for elasticizing said gutters comprises lengths of elastic material which are attached to the garment structure in only said waistband regions of said gutters.

17. The disposable waste containment garment of claim 1 wherein said crotch region of said core is sufficiently more rigid than said waistband regions of said core such that said elasticized gutters tend to induce transverse folds in the garment intermediate said crotch region of the garment and said waistband regions of the garment.

18. A disposable waste containment garment having a rear waistband region, a front waistband region, and a crotch region, said garment comprising:

a body member having a generally rectangular plan form, a width less than ½ the girth of a user of the garment, and comprising a liquid permeable, rectangular-shaped topsheet, a liquid impervious backsheet having a rectangular-shape, and an absorbent pad disposed intermediate said topsheet and said backsheet, said backsheet having a width sufficiently greater than the width of said topsheet to provide longitudinally extending side-gutter-forming edge portions outboard from the longitudinal edges of said topsheet, said backsheet being U-folded about the longitudinal side edges of said body member so that said edge portions overlie longitudinal side edge regions of said topsheet, said edge portions and said side edge regions being secured together in a face-to-face relation only in the waistband regions of the garment and in the attachment zone that is disposed adjacent each longitudinal edge of the garment intermediate said waistband regions, and means for elasticizing said edge portions adjacent their distal edges;

four stub belts, a stub belt secured to and extending laterally outwardly from each corner of said body member; and means for securing said belts together in pairs to secure the garment on a user.

19. The disposable waste containment garment of claim 1 or 18 wherein the width of said crotch region of said absorbent core is less than the lateral span intermediate said distal edges when the garment is flat out and uncontracted.

* * * * *